(12) United States Patent
Golden et al.

(10) Patent No.: US 10,349,924 B2
(45) Date of Patent: Jul. 16, 2019

(54) PERCUTANEOUS ASPIRATING CANNULA

(71) Applicant: Adimend Biosciences, LLC, San Antonio, TX (US)

(72) Inventors: Joe Golden, San Antonio, TX (US); Pendleton Wickersham, San Antonio, TX (US)

(*) Notice: Subject to any disclaimer, the term of this patent is extended or adjusted under 35 U.S.C. 154(b) by 0 days.

(21) Appl. No.: 15/606,641

(22) Filed: May 26, 2017

(65) Prior Publication Data

US 2017/0258459 A1 Sep. 14, 2017
US 2018/0199923 A9 Jul. 19, 2018

Related U.S. Application Data

(63) Continuation of application No. 15/502,814, filed as application No. PCT/US2015/039833 on Jul. 9, 2015.

(60) Provisional application No. 62/092,022, filed on Dec. 15, 2014, provisional application No. 62/022,511, filed on Jul. 9, 2014.

(51) Int. Cl.
*A61B 10/02* (2006.01)
*A61M 5/32* (2006.01)
*A61M 5/19* (2006.01)
*A61M 5/31* (2006.01)

(52) U.S. Cl.
CPC ...... *A61B 10/0283* (2013.01); *A61B 10/0275* (2013.01); *A61M 5/19* (2013.01); *A61M 5/3134* (2013.01); *A61M 5/3293* (2013.01)

(58) Field of Classification Search
CPC ............ A61M 5/19; A61M 2005/1787; A61B 10/0283
See application file for complete search history.

(56) References Cited

U.S. PATENT DOCUMENTS 3,094,122 A * 6/1963 Gauthier ........... A61M 25/0014
604/164.01
3,978,846 A * 9/1976 Bailey ................ A61B 5/15003
600/575
4,253,501 A 3/1981 Ogle
(Continued)

FOREIGN PATENT DOCUMENTS

EP 2875836 A1 5/2015
WO 2013070259 5/2013

OTHER PUBLICATIONS

EmCyte CorporationProduct Catalog; Copyright 2012.
(Continued)

*Primary Examiner* — Emily L Schmidt
(74) *Attorney, Agent, or Firm* — John C. Cave; Gunn, Lee & Cave, P.C.

(57) ABSTRACT

The dual syringe with percutaneous cannula is a medical device for harvesting and transferring cells for autologous transplantation without the requirement of a surgical setting or ambulatory care. The dual syringe is a closed sterile system that allows for the harvesting syringe to harvest the cells/tissue from a first location of a patient which is then centrifuged to aggregate the cells. The aggregated cell pellet is transferred to a transfer syringe. The cell pellet is then reinjected by the transfer syringe into the patient at a second location for therapeutic purpose. The percutaneous cannula permits insertion of a cannula, with the assistance of a needle, without the need of a surgical incision or trocar.

26 Claims, 11 Drawing Sheets

(56) References Cited

U.S. PATENT DOCUMENTS

| | | | |
|---|---|---|---|
| 5,199,949 A | 4/1993 | Haber | |
| 8,052,969 B2 | 11/2011 | Buhr | |
| 8,591,391 B2 | 11/2013 | Chavarria | |
| 8,622,997 B2 | 1/2014 | Shippert | |
| 2004/0204688 A1* | 10/2004 | Lin | A61M 5/3232 604/192 |
| 2006/0097013 A1 | 5/2006 | Bargh | |
| 2007/0088282 A1 | 4/2007 | Ranalletta | |
| 2008/0167621 A1* | 7/2008 | Wagner | A61M 5/19 604/191 |
| 2010/0082015 A1 | 4/2010 | Chebator | |
| 2010/0249727 A1 | 9/2010 | Thorne, Jr. | |
| 2011/0118659 A1 | 5/2011 | Maaskamp | |
| 2012/0156177 A1 | 6/2012 | Scarpone | |
| 2014/0099288 A1 | 4/2014 | Dunworth et al. | |

OTHER PUBLICATIONS

Terumo BCT, Inc. brochure; Copyright 2012.

FDA Premarket Notification 510(k) Summary; Lipose Fat Transfer System; Lipose Corp.; Dec. 4, 2008.

FDA Premarket Notification 510(k) Summary; NIPRO Disposable Syringe; Nipro Medication Corporation; Apr. 30, 2009.

FDA Premarket Notification 510(k) Summary; DMC Medical Single-Use Polycarbonate Syringe; DMC Medical Ltd.; Apr. 6, 2011.

FDA Premarket Notification 510(k) Summary; Harvest AdiPrep Adipose Transfer System; Harvest Technologies Corporation; Sep. 18, 2012.

FDA Premarket Notification 510(k) Summary; HydraSolve Lipoplasty System; Andrew Technologies; Jan. 17, 2013.

Neogenesis Unistation product information website page located at http://www.neogenesis.co.kr/eng/sub/sub2_view.php?bo_table=eboard2_1&wr_id+1; Copyright 2016.

StromaCell Mechanical Cell Separation brochure; MicroAire Surgical Instruments; Copyright 2013.

Tulip Medical, Tulip Cell-Friendly Cannulas product information website page http://www.tulipmedical.com/tulip-product-cannulas-general.html; Copyright 2017.

Resolve System—Materials flyer; LifeCell Corporation; Copyright 2014.

SmartPrep 2 brochure; Harvest Technologies Corporation; Copyright 2010.

ThermoGenesis Corporation brochure identifying Res-O 60 PRP System; Copyright 2012.

Fuerst Ittleman Power Point Presentation Slides; Copyright 2012.

INDEPTH Fat Chance article by WNDY LEWIS located at http://www.plasticsurgerypractice.com/2013/12/indepth-fat-chance; published on Dec. 26, 2013.

Millennium Surgical Corp., Liposuction Surgical Instruments product information website page located at https://www.surgicalinstruments.com/cosmetic-and-plastic-surgery/liposuction-surgical-instruments; Copyright 2017.

PCT International Search Report for International Application No. PCT/US15/39833 dated Oct. 26, 2015, related to the present application.

Harvest Adiprep Adipose Concentration System brochure; Harvest Technologies (publically used, on sale or otherwise available to the public prior to Dec. 15, 2014).

ACP Double Syringe System brochure; Arthrex (publically used, on sale or otherwise available to the public prior to Dec. 15, 2014).

BioCUE Platelet Concentration System flyer; BloMet Biologics (publically used, on sale or otherwise available to the public prior to Dec. 15, 2014).

Harvest Adiprep Adipose Concentration System brochure; Harvest Technologies Corp, (publically used, on sale or otherwise available to the public prior to Dec. 15, 2014).

Regulatory Assessment memo; ThermoGenesis Corporation (publically used, on sale or otherwise available to the public prior to Dec. 15, 2014).

RES-Z60 BMC Point-of-care automated cell capturing system brochure; Totipotent SC (publically used, on sale or otherwise available to the public prior to Dec. 15, 2014).

Res-Q 60 BMC literature; ThermoGenesis Corporation (publically used, on sale or otherwise available to the public prior to Dec. 15, 2014).

Res-Q 60 BMC literature; Bone Marrow Concentration System, System Overview; ThermoGenesis Corporation (publically used, on sale or otherwise available to the public prior to Dec. 15, 2014).

Tulip GEMS flyer; Premium Single-Use CellFriendly Instruments (publically used, on sale or otherwise available to the public prior to Dec. 15, 2014).

Tulip GEMS Single-Use Instruments product information website page located at https://web.archive.org/web/20150301013331/http://www.tulipmedical.com:80/tulip-gems-Instruments.html (publically used, on sale or otherwise available to the public prior to Dec. 15, 2014).

Fuerst Ittleman Power Point Presentation Slides; Copyright 2012 (publically used, on sale or otherwise available to the public prior to Dec. 15, 2014).

Wells Johnson Company, Aspiration Cannulas product information website page located at http://www.wellsgrp.com/index.php?option=com_rokecwid&Itemid=75#l/Aspiration-Cannulas/c/788907/offset=0&sort=normal (publically used, on sale or otherwise available to the public prior to Dec. 15, 2014).

* cited by examiner

PERCUTANEOUS ASPIRATING CANNULA

CROSS-REFERENCES TO RELATED APPLICATIONS

This application claims the benefit of U.S. application Ser. No. 15/502,814 filed Feb. 9, 2017 entitled "Dual Syringe with Percutaneous Cannula," PCT Application Serial No. PCT/US2015/039833 filed Jul. 9, 2015 entitled "Dual Syringe with Percutaneous Cannula," U.S. Provisional Application Ser. No. 62/092,022 filed Dec. 15, 2014 entitled "Percutaneous Aspirating Cannula," and U.S. Provisional Application Ser. No. 62/022,511 filed Jul. 9, 2014 entitled "Dual Syringe," which are all incorporated by reference herein.

STATEMENT REGARDING FEDERALLY SPONSORED RESEARCH OR DEVELOPMENT

Not applicable.

1. FIELD OF THE INVENTION

The present invention relates to the field of medical devices, specifically syringes and aspirating cannulas.

2. BACKGROUND OF THE RELATED ART

Autologous stem cell transplant generally occurs in a highly sterile environment such as available in an operating room or ambulatory surgical center. One of the common methods to obtain stem cells is through the use of aspirating cannulas. However, cannulas require a second instrument to access the interior of the body for collection of the stem cells. For example, extraction of bone marrow stem cells generally requires the insertion of a trocar and the cannula after the trocar is in place. Similarly, extraction of stem cells from adipose tissues generally requires a scalpel incision into the patient before insertion of the aspirating cannula. Moreover, once the desired cells and tissues are harvested by the cannula, the cells or tissues are then transferred to syringes or test tubes. These transfers significantly increase the opportunity for sterile breaks through introduction of manual transfers. An invention and method is desired to simply extract and collect desired cells from a patient in a sterile closed system and then reintroduce the concentrated cells for therapeutic purpose.

The present invention simplifies the process for autologous stem cell transplant by utilization of a dual syringe with percutaneous aspirating cannula that safely harvests cells and tissues without the need for a surgical procedure and by minimizing the opportunity for a sterile break. The percutaneous aspirating cannula utilizes a needle and a tapered edge cannula wherein the needle and tapered edge allow for the percutaneous aspirating cannula to be inserted directly into a patient without the need of surgical incision or insertion of a trocar. The dual syringe is a closed system that allows for the harvesting syringe to harvest the cells/tissue which is then centrifuged to aggregate the cells wherein the isolated cell pellet is then transferred to a second syringe where it can then be reinjected to the patient for a desired therapeutic purpose.

DETAILED DESCRIPTION OF THE VARIOUS EMBODIMENTS

As seen in FIGS. 1 through 6 and 12, the dual syringe 1 comprises a harvesting syringe 10 and a transfer syringe 100. The harvesting syringe 10 comprises a barrel 20, spacer 70, and harvesting plunger 90. The barrel 20 comprises a partially cylindrical sidewall 21 and bottom wall 30 that define an interior cavity 60. The side wall 21 is shaped so that it forms a hemi-cylindrical groove 22 that extends from the top end 23 of the harvesting syringe 10 to the bottom end 24. The preferred embodiment of the groove is hemi-cylindrical but other shapes such as triangular or rectangular are envisioned. On the opposing end of the barrel 20 from the bottom wall 30 is an opening 40. Handles 25 extend perpendicularly from the cylindrical sidewall 21 and away from the opening 40 at the top end 23 of the barrel 20. The handles 25 are positioned 90 degrees from the hemi-cylindrical groove 22.

The interior surface 26 is of the cylindrical sidewall 21 is generally smooth and corresponds in shape to the exterior surface 27 which includes the hemi-cylindrical groove 22. A ridge 28 is located along the interior surface 26 of the cylindrical sidewall 21 near the top end 23. The cylindrical sidewall 21 is generally translucent and contains identifying markings 29 to indicate the volume of material within the interior cavity 60.

Still referring to FIGS. 1 through 6 and 12, a tubular shaped spacer 70 having a cylindrical sidewall 71, a bottom wall 72, and top wall 73 is positioned within the hemi-cylindrical groove 22 such that the bottom wall 72 of the spacer 70 and bottom wall 30 of the harvesting syringe 10 are aligned. The top wall 73 of the spacer 70 is positioned approximately at the midpoint of the hemi-cylindrical groove 22 of the harvesting syringe 10. An interior channel 74 extends from the top wall 73 to the bottom wall 72 of the spacer 70. A top port 75 is positioned on the top wall 73 which creates a fluid pathway with channel 74. A syringe locking mechanism 76 having a channel 78 through its center is positioned on the top wall 73 above the top port 75. The syringe locking mechanism 76 may be female luer taper connection. A bottom port 77 is positioned on the bottom wall 72. A fluid pathway exists from the bottom port 76, through the channel 74, through the top port 75 and through the channel 78 of the syringe locking mechanism 76. The spacer 70 may be bonded, glued, or welded onto the barrel 20. Alternatively, the spacer 70 and barrel 21 may be integral.

The harvesting syringe 10 has an outflow port 31 positioned approximately in the middle of the of the bottom wall 30 and an inflow port 32 positioned in a portion of the bottom wall 30 opposite from the spacer 70 and aligned with the bottom port 77 and the outflow port 31. Both the inflow port 31 and outflow port 31 create a fluid pathway into the interior cavity 60 of the barrel 20. A needle attachment 34, positioned on the exterior surface 33 of the bottom wall 30, has a channel 41 through its center such that a fluid pathway exists with the inflow port 32. The needle attachment 34 may be a male luer taper connection. On the exterior surface 33 of the bottom wall 30 a transfer wall 35 is formed around the outflow port 31 and transfer port 77. A transfer cover 36 is attached to the transfer wall 35 and covers the outflow port 31 and transfer port 77. The transfer wall 35 and transfer cover 36 create a pathway 38 between the outflow port 31 and transfer port 77.

Figures 1, 2:
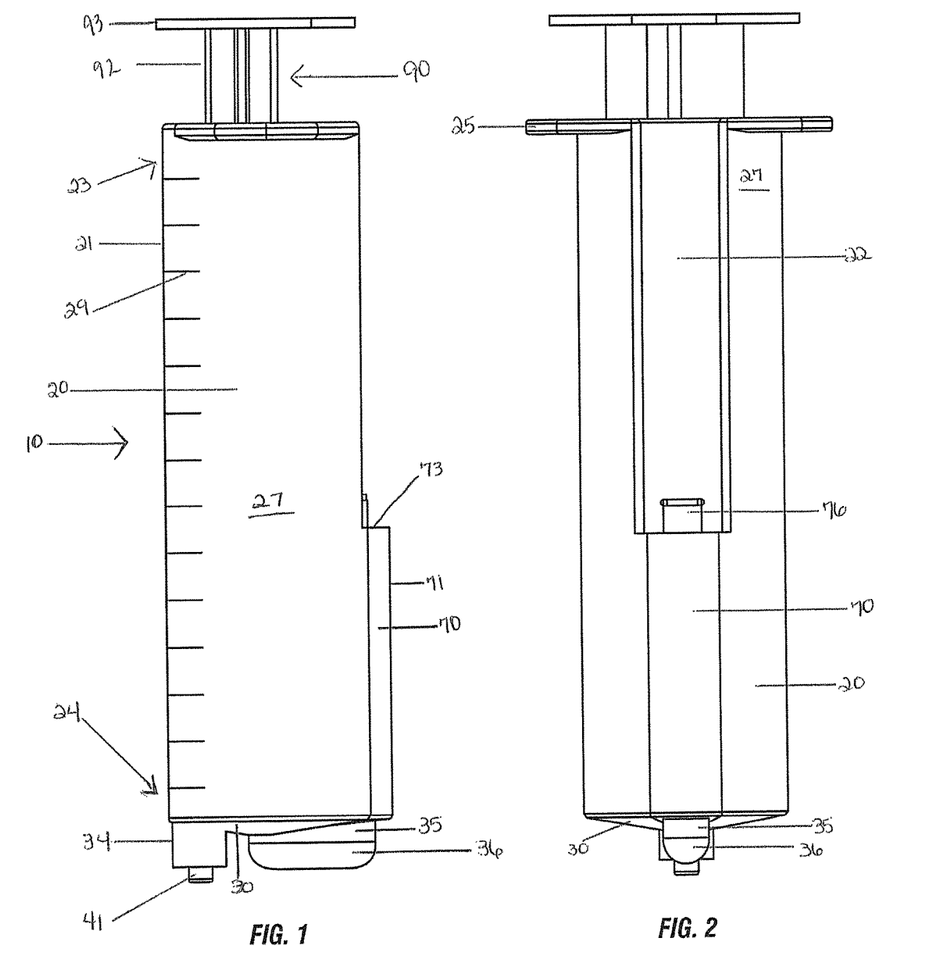
FIG. 1 is a side profile of the harvesting syringe.
FIG. 2 is a front profile of the harvesting syringe.
Figure 3:
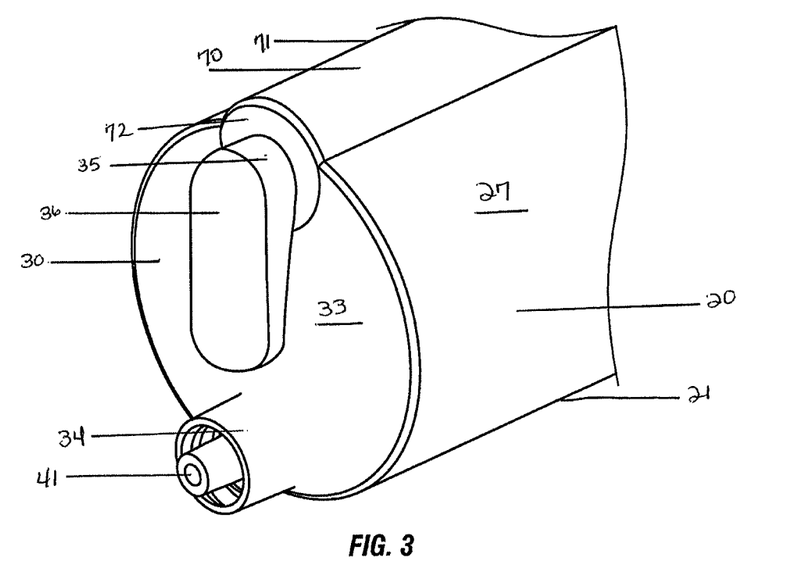
FIG. 3 is an isometric view showing the bottom of the dual syringe.
Figure 4:
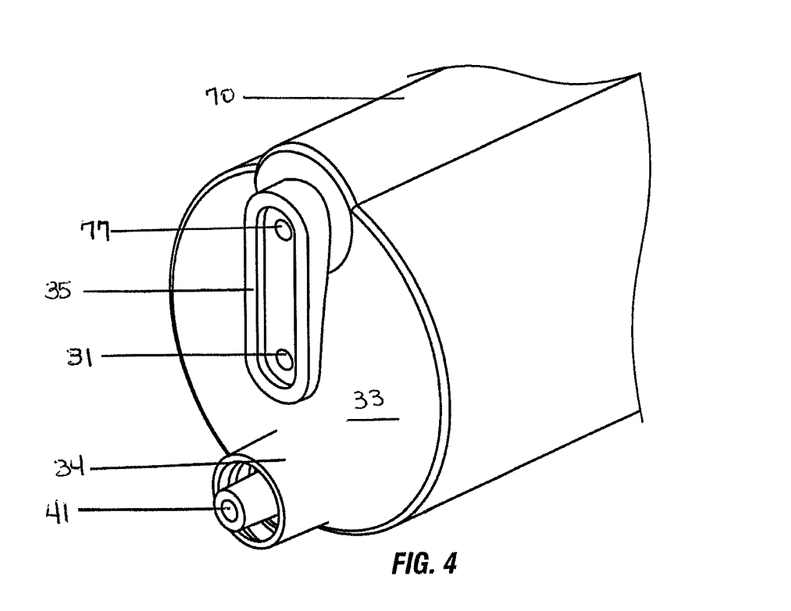
FIG. 4 is an isometric view showing the bottom of the dual syringe with the transfer covering removed.
Figure 5:
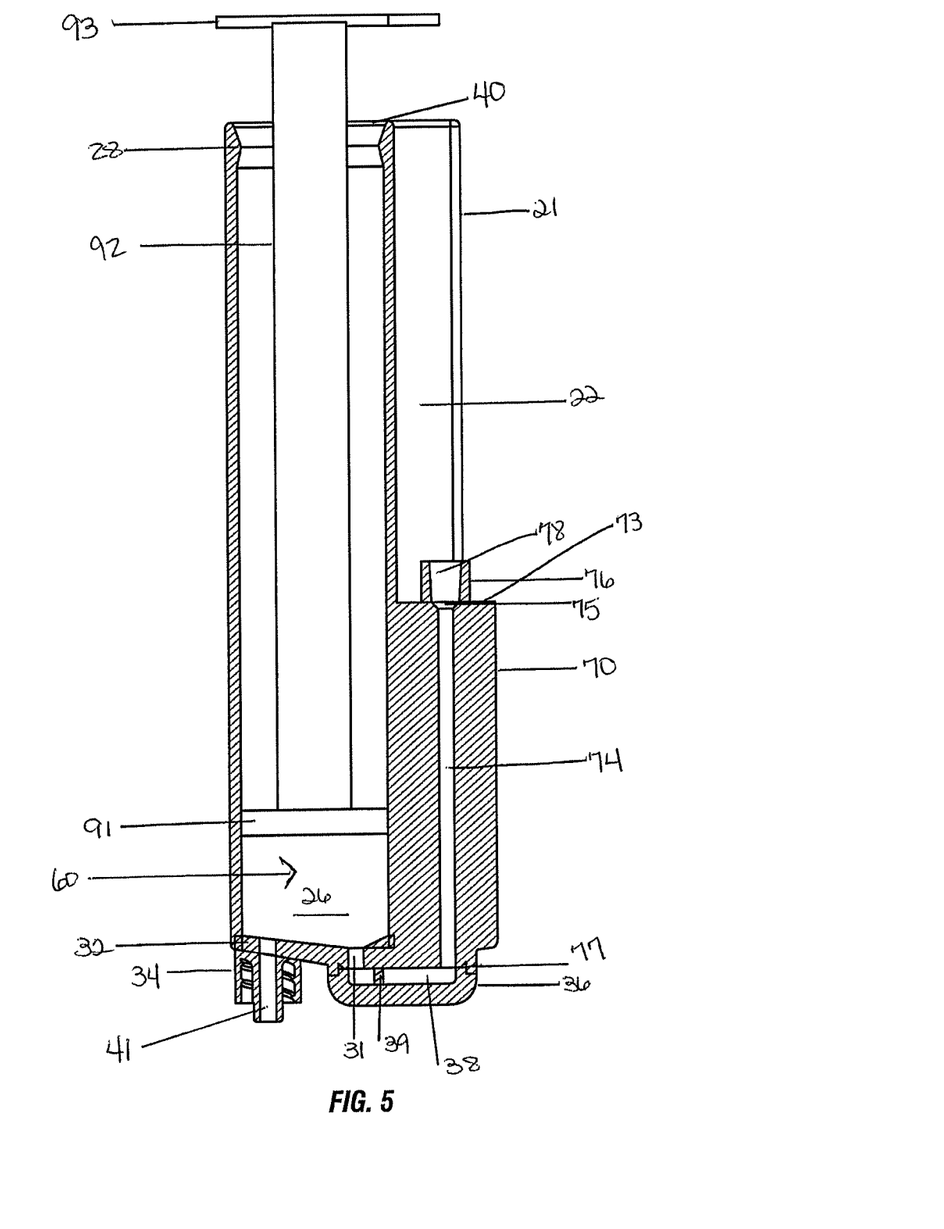
FIG. 5 is a cross section of the side profile of the harvesting syringe.
Figure 6:
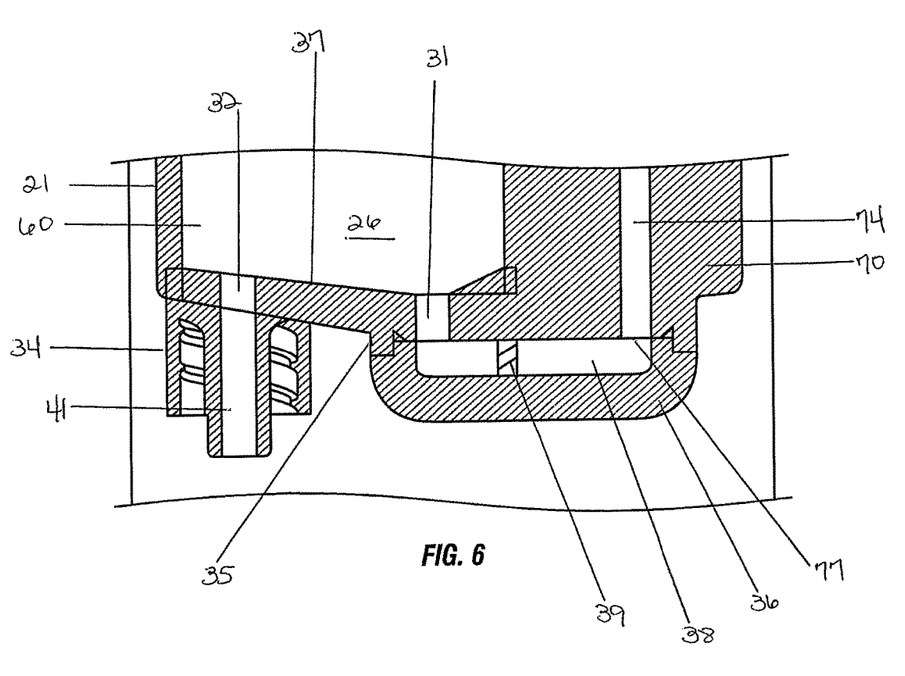
FIG. 6 is a close-up cross section of the side profile of the lower end of the harvesting syringe.

As seen in FIGS. 5 and 6, the interior surface 37 of the bottom wall 30 is sloped such that the interior surface 37 is shaped to funnel contents into the outflow port 31. The exterior surface 33 of the bottom wall 30 corresponds to the same slope of the interior surface 37. The pathway 38 may be selectively closed by a valve 39.

The harvesting plunger 90 has a stopper or harvesting plunger head 91 connected to one end of a shaft 92. The opposing end of the shaft 92 has a handle 93 which is shaped to generally correspond with the interior surface 26 of the cylindrical sidewall 31, including the hemi-cylindrical groove 22. The harvesting plunger head 91 is shaped to correspond with the interior surface 26 of the cylindrical sidewall 31 including the hemi-cylindrical groove 22. The shaft 92 is screwed into the plunger head 91 and the friction created by the plunger head 91 and the interior surface 26 generally holds the plunger head 91 in place which allows the shaft 92 to be screwed in or out. The harvesting plunger head 91 is made of a malleable material such as a hard rubber to create a seal between the interior cavity 60 of the barrel 20 and the atmospheric environment existing above the plunger head 91. The ridge 28 on the interior surface 26 inhibits removal of the harvesting plunger head 91 from the interior cavity 60 of the barrel 20.

Figure 12:
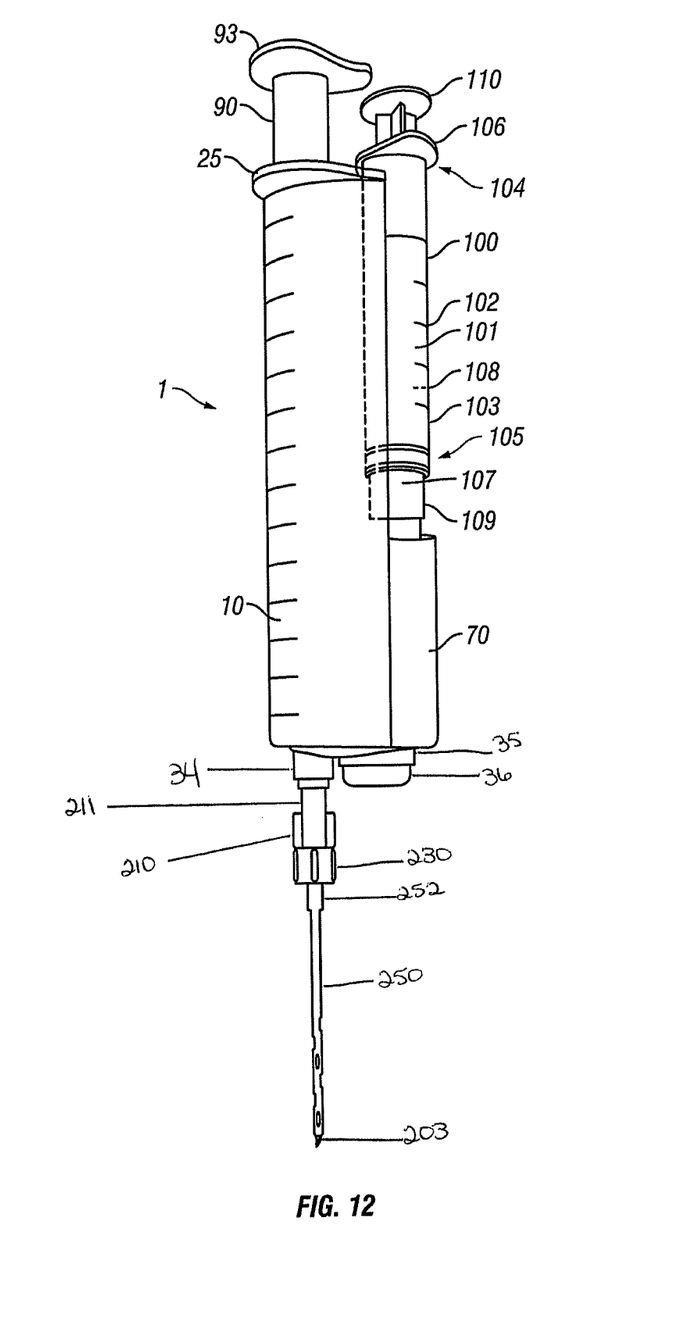
FIG. 12 is an isometric view of the dual syringe with the percutaneous cannula assembly.

As seen in FIG. 12, the transfer syringe 100 comprises a barrel 101 and a transfer plunger 110. The barrel 101 is translucent and contains identifying markings 102 to indicate the volume of material within the barrel 101. The transfer syringe barrel 101 comprises a cylindrical sidewall 103 having an open top end 104 and a closed bottom end 105. A handle 106 extends from the barrel 101 at its top end 104. A port 107 is positioned in the bottom end 105 of the syringe barrel 101 to allow access into the interior cavity 108 of the barrel 101. A needle attachment 109 having a channel through its center is affixed to exterior surface of the bottom end 105. The needle attachment 109 may be a male luer taper connection. A fluid pathway exists between the channel of the needle attachment 109, port 107, and interior cavity 108.

Figure 7:
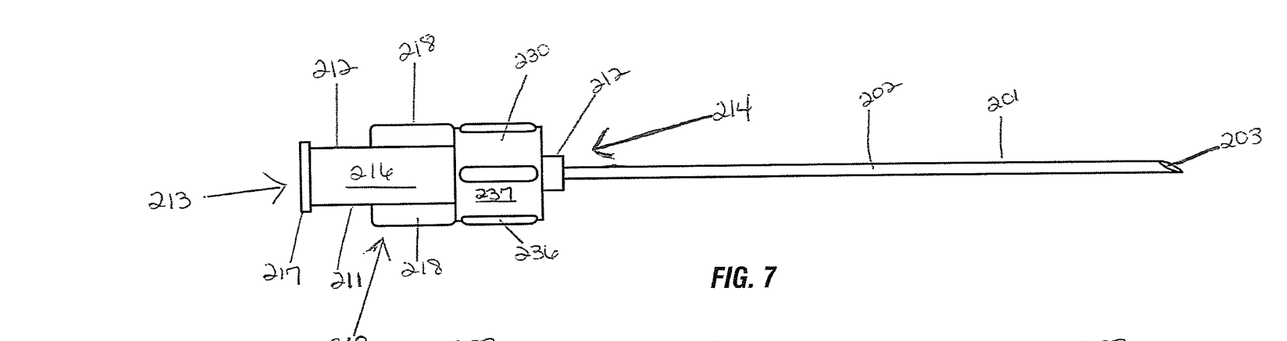
FIG. 7 is a profile view of the needle hub assembly.
Figure 9:
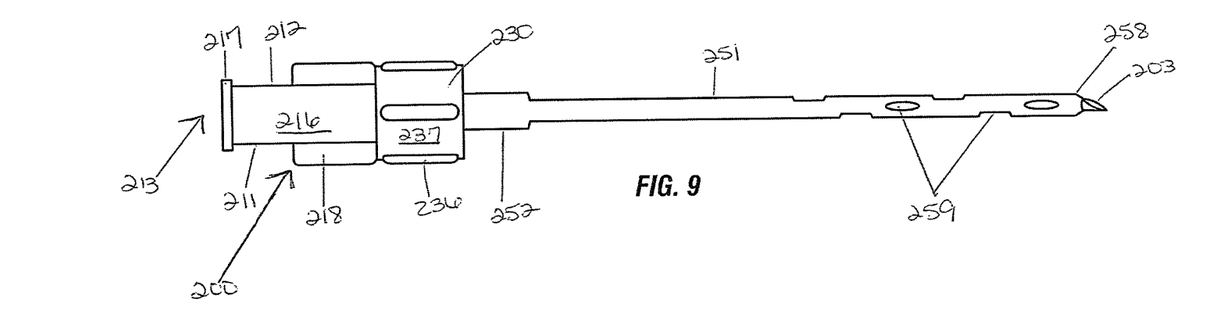
FIG. 9 is a profile view of the percutaneous cannula.
Figure 10:
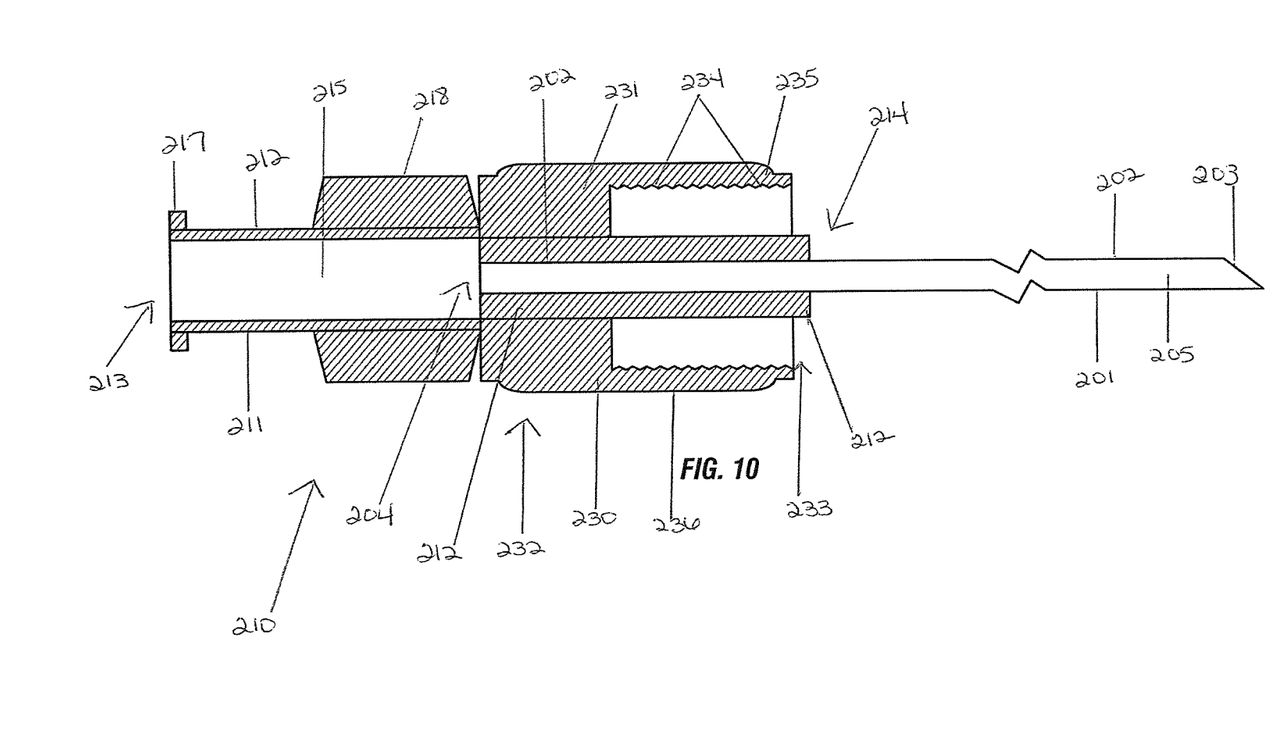
FIG. 10 is a close-up cross section of the side profile of the needle hub assembly.

As seen in FIGS. 9 and 12, the percutaneous cannula assembly 200 is composed of a needle hub 210, a needle 201, and a removable cannula 250. As seen in FIGS. 7 and 10, the hollow tubular needle 201 is comprised of cylindrical sidewall 202 having a beveled point 203 on one end and an opening 204 on the opposing end. A cavity 205 is formed by the cylindrical sidewall 202 and extends from the beveled point 203 to the opening 204.

As seen in FIGS. 7, 9, 10, and 12, the needle hub 210 contains a syringe connecting portion 211 and a cannula connecting portion 230. The syringe connecting portion 211 consists of a cylindrical sidewall 212 having a connecting outlet 213 on one end and a needle receiving outlet 214 on the opposing end. A radial flange 217 is positioned around the connecting outlet 213 on the exterior face 216 of the cylindrical sidewall 212. The radial flange 217 may be consistent with a female luer taper connection. A cavity 215 is formed by the cylindrical sidewall 212 and extends from the connecting outlet 213 on one end and a needle receiving outlet 214. The needle 201 is permanently affixed to at least a portion of the interior face of the cylindrical sidewall 212. Two wings 218 extend radially away from the exterior face 216 of the cylindrical sidewall 212. The wings 218 permit a user to grip and rotate the needle hub 210. The wings 218 are positioned on the exterior face 216 of the cylindrical sidewall 212 at a sufficient distance away from the radial flange 217 to allow the radial flange 217 to connect to the needle attachment 34 and be screwed or positioned into place. A fluid communication pathway exists from the connecting outlet 213 to the beveled point 203 of the needle 201.

Figure 8:
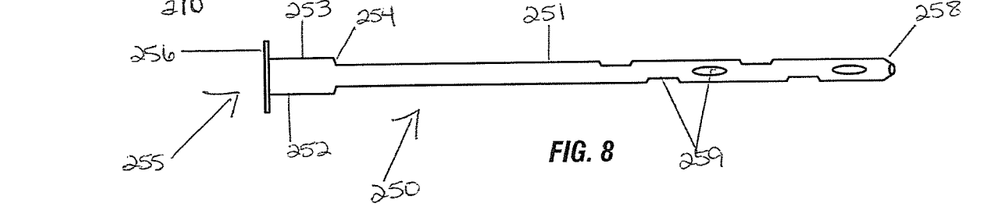
FIG. 8 is a profile view of the cannula.

As seen in FIG. 8, the cannula connecting portion 230 consists of a cylindrical sidewall 231 having a connecting end 232 on one end and a cannula receiving end 233 on the opposing end. The diameter of the cylindrical sidewall 231 of the cannula connecting portion 230 is greater than the cylindrical sidewall 212 of the syringe connecting portion 211. The connecting end 232 is attached to the exterior face 216 of the cylindrical sidewall 212 of the syringe connecting portion 211 at the approximate midpoint of the cylindrical sidewall 212 of the syringe connecting portion 211. Threads 234 are positioned on the interior face 234 of the cylindrical sidewall 231 of the cannula connecting portion 230. Threads 234 may be consistent with a male luer lock taper connection. Radial ridges 236 are positioned on the external face 237 of the cylindrical sidewall 231 of the cannula connecting portion 230. The radial ridges 236 assist in gripping the needle hub 210.

The distance between the interior face 234 of the cylindrical sidewall 231 of the cannula connecting portion 230 and the exterior face 216 of the cylindrical sidewall 212 of the syringe connecting portion 211 is of sufficient distance that a cannula or other syringe may be removably attached to the needle hub 210.

As seen in FIG. 8, the cannula 250 is comprised of a tubular shaft 251 attached to a cannula hub 252. The cannula hub 252 is tubular in shape with a generally cylindrical sidewall 253 with a cannula receiving portion 254 on one end and outlet 255 on the opposing end. A radial flange 256 is positioned around the outlet 255 of the cylindrical sidewall 253. The radial flange 256 may be consistent with a female luer taper connection. One end of the tubular shaft 251 is attached to the cannula hub 252 at the cannula receiving portion 254. The other end of the tubular shaft 251 is a tapered outlet 258. The cylindrical sidewall 253 and cannula shaft 251 form a cavity 257 between the outlet 255 and the tapered outlet 258. The cannula shaft 251 and the tapered outlet 258 have an inner diameter large enough to allow the needle 201 to pass through. Ports 259 extend longitudinally through the sidewall of the tubular shaft 251. Ports 259 may have smooth edges for minimal tissue cleavage or sharp skived edges for maximum tissue recovery depending on the desired use and desired tissue and/or cells to harvest. Ports 259 may be oriented on one side or may extend generally around the circumference of the tubular shaft 251. Depth markings are positioned along the outer face of the cannula shaft 251 that indicate the distance from the respective marking to the tapered outlet 258.

As seen in FIGS. 11 through 14, the transfer syringe 100 is attached to the harvesting syringe 10 through attachment of the needle attachment 109 to the syringe locking mechanism 76 of the spacer 70. The barrel 101 of the transfer syringe 100 partially fits within the hemi-cylindrical groove 22 of the harvesting syringe 10. The harvesting plunger head 91 is shaped to not interfere with the transfer syringe 100 or to prohibit the screwing in of the transfer syringe 100 onto the syringe locking mechanism 76. A pathway is created between the interior cavity 60 of the harvesting syringe 10 and the interior cavity 108 of the transfer syringe 100 by the outflow port 31, pathway 38, bottom port 77, interior cavity 74 of the spacer 70, top port 75, needle attachment 109, and port 107. The pathway 38 may be selectively closed by a valve 39. Valve 39 may designed as a pressure sensitive valve which seals with positive pressure from outflow port 31 but opens upon negative pressure from the bottom port 77.

Figure 13:
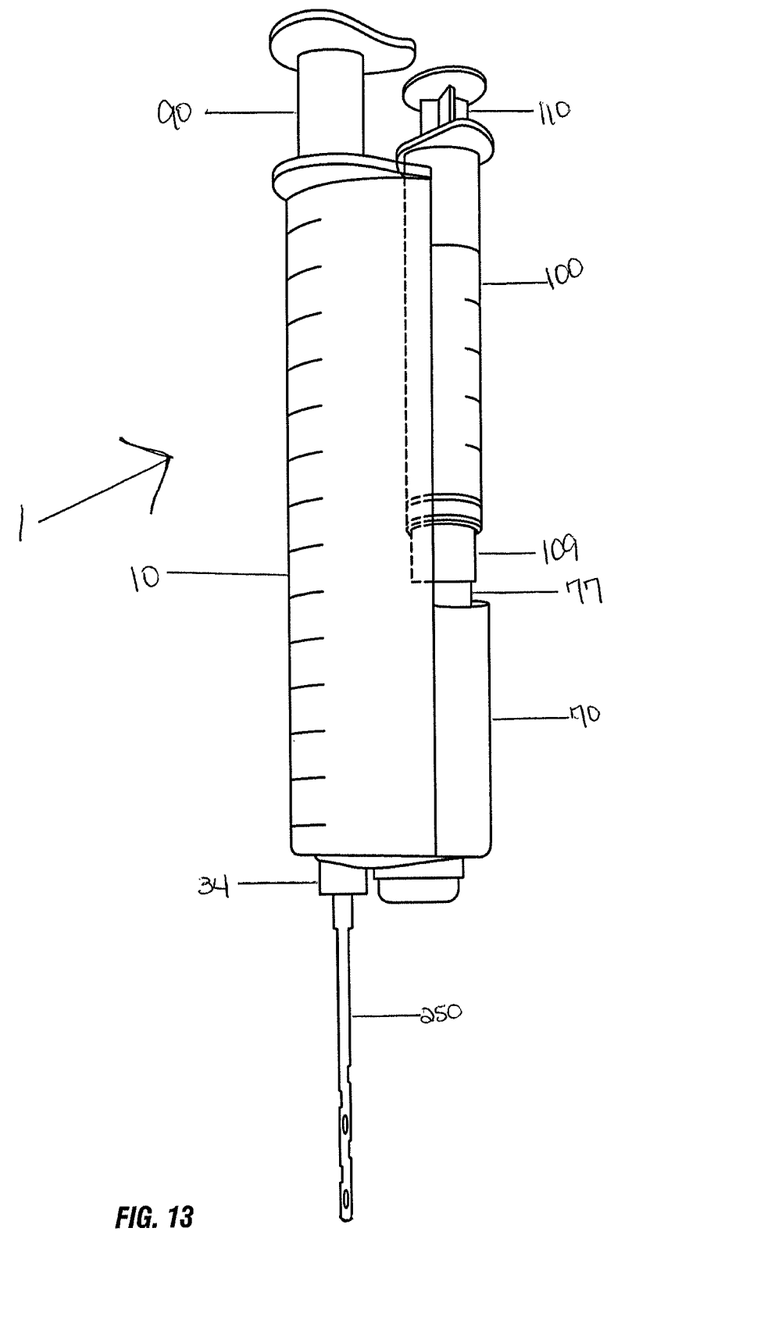
FIG. 13 is an isometric view of the dual syringe with the cannula.

As seen in FIG. 12, the needle hub 210 may attach to the dual syringe 1 through mating of needle attachment 34 of the dual syringe 1 and ridge 217 of the needle hub assembly 210. The cannula 250 may attach to the needle hub 210 through mating of the cannula connecting portion 230 and radial flange 256 of the cannula 250. As seen in FIGS. 9 and 12, the needle 201 extends out the tapered outlet 258 of the cannula 250 when the cannula 250 is attached to the needle hub 210. As seen in FIG. 13, the cannula 250 may also attach to the dual syringe 1 through mating of needle attachment 34 of the dual syringe 1 and radial flange 256 of the cannula 250. In the preferred embodiment, the attachments are luer lock taper connections although alternative embodiments may use a luer slip taper connection.

Figure 11:
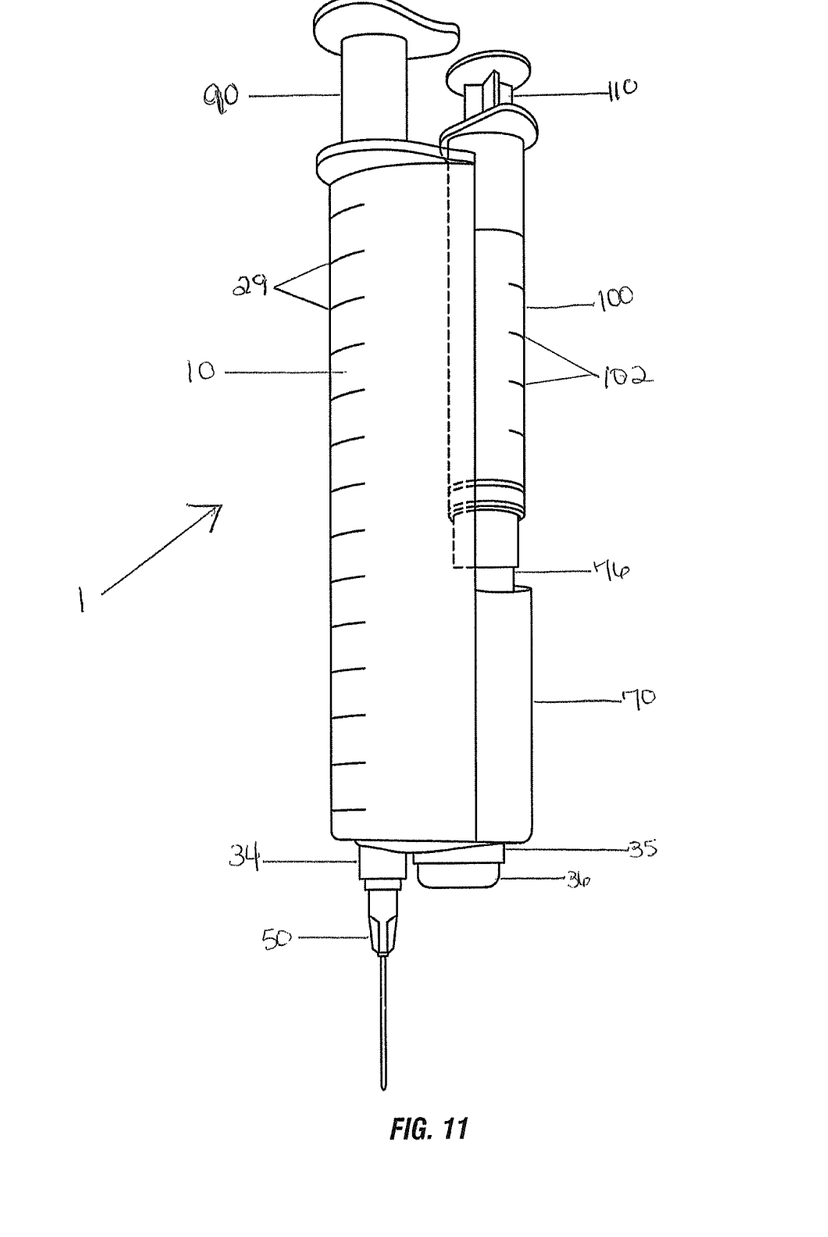
FIG. 11 is an isometric view of the dual syringe with a standard hypodermic needle.
Figure 15:
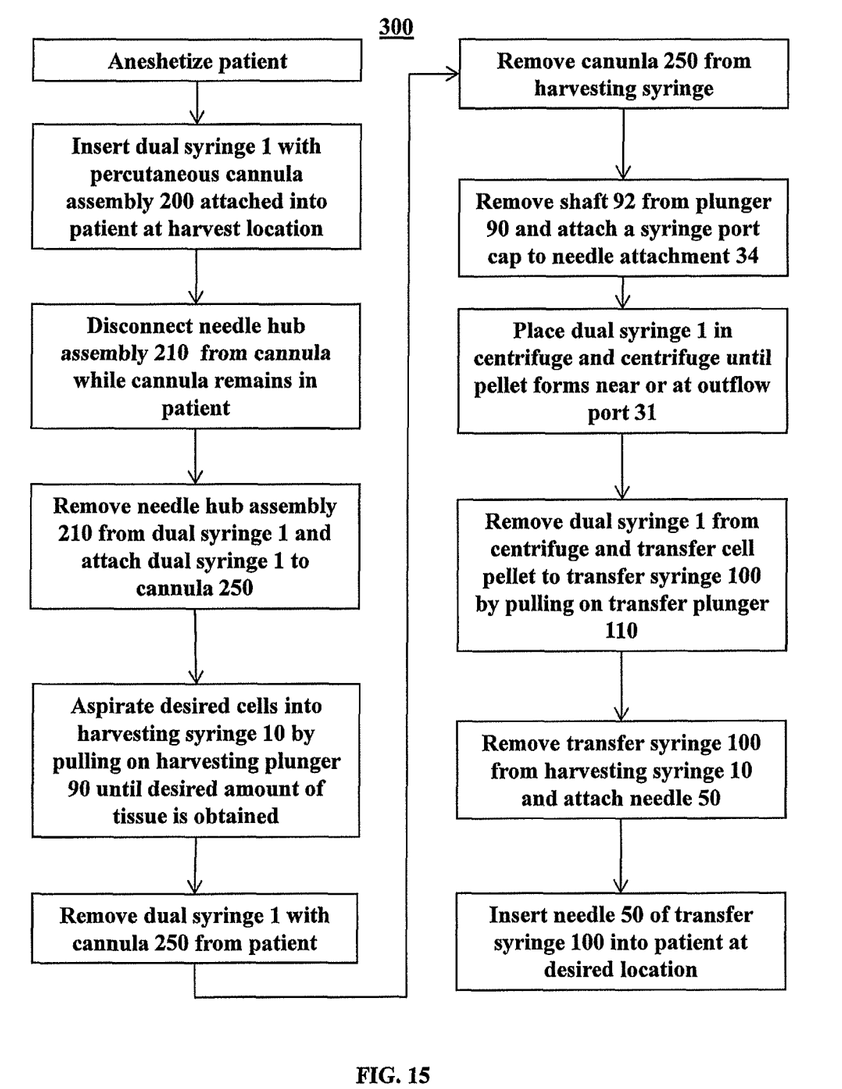
FIG. 15 is a flow chart of the method of autologous stem cell transplant.

Referring to FIG. 15, the broad process 300 of operation of the dual syringe 1 comprises the following steps:

Anesthetize the patient generally or locally where cells are to be harvested. Anesthetization may occur through use of the dual syringe 1 with a standard hypodermic needle 50 attached as seen in FIG. 11, or through the percutaneous adipose aspirating cannula 200 as seen in FIG. 12. Anesthetizing agent is drawn into the harvesting syringe 10 by pulling on the harvesting plunger 90. The anesthetizing agent is drawn through the standard hypodermic needle 50 or percutaneous adipose aspirating cannula 200. The anesthetic agent is then applied locally at the site of cell harvesting.

The dual syringe 1, with the attached transfer syringe 100 (with the transfer plunger 110 fully depressed) and the percutaneous cannula assembly 200, is inserted into tissue or bone of a patient to harvest the desired cells. The beveled point 203 of the needle 201 along with the cannula 250 inserts percutaneously through patient's skin and advanced into the patient until the appropriate depth as indicated by the depth markings on the cannula 250. The tapered outlet 255 of the cannula 250 assists insertion into the patient's skin to reduce any catching or blunt trauma.

Once the desired depth is obtained, the cannula 250 is unmated from the needle hub assembly 210 which allows for the removal of the dual syringe 1 (with the needle hub assembly 210 still attached) from the cannula 250. The needle hub assembly 210 is unmated from the harvesting syringe 10. The harvesting syringe is then attached to the cannula 250 through mating the needle attachment 34 of the dual syringe 1 and ridge 256 of the cannula 250. This establishes a fluid communication pathway from the tapered outlet 258 and ports 259, through the tubular shaft 251, through the cannula hub 252, through the outlet 255, through the inflow port 32, and into the barrel 20 of the harvesting syringe 10.

The cannula 250 may then be used as a standard aspirating cannula to harvest the desired cells. The user creates negative pressure within barrel 20 by pulling on the harvesting plunger 90 to draw in cells and tissues while simultaneously moving the cannula within the patient's body at the desired location. As the cannula 250 is moved back and forth while inside the patient, the ports 259 and tapered outlet 258 shear and collect cells/tissue which are then drawn into the cannula 250 and are ultimately drawn into the barrel 20.

Once the desired volume of cells and/or tissues are harvested, the harvesting syringe 10 (with the cannula 250 still attached) is removed from the patient.

The cannula 250 is removed 270 from the harvesting syringe 10. The shaft 92 is unscrewed from the plunger head 91 and removed from the harvesting syringe 10. A standard syringe port cap is attached to the needle attachment 34 to seal inflow port 32. The cap ensures sterility and prevents migration of the cell pellet into the inflow port 32.

The dual syringe 1 is placed in a centrifuge and spun at approximately 500 to 2000 g forces for a period of 3 to 20 minutes. Centrifugation causes the aspirated cells to separate from the aspirated fluid. As a result of the funnel shape of the bottom wall 30, the cells, denser than the fluid, form a pellet on the bottom wall 30 near the outflow port 31. The valve 39 remains closed due to the positive pressure exerted from the outflow port 31 which prevents any of the contents of the barrel from migrating through pathway 38 and/or through the bottom port 77 of the spacer 70.

The dual syringe 1 is removed from the centrifuge. The transfer plunger 110 is pulled away from the bottom end 105 which creates negative pressure within the interior cavity 108 of the transfer syringe 100. This negative pressure opens the valve 39 to allow cells of the pellet to move through the outflow port 31, through the pathway 38, through the interior cavity 74 of the spacer 70, through the top port 75, through the port 107 of the transfer syringe and into the interior cavity 108 of the transfer syringe 100. To adjust for the varying hydraulic pressure within the interior cavity 60 of the harvesting syringe 10, if necessary, the harvesting plunger may be manually depressed, after reattachment of the shaft 92, by the user in conjunction with user's pulling of the transfer plunger 110.

Figure 14:
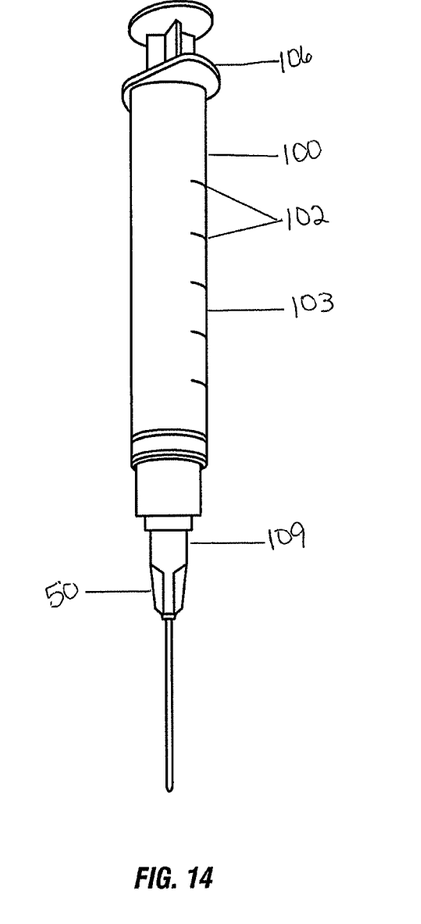
FIG. 14 is an isometric view of the transfer syringe with a standard hypodermic needle.

Once the cell pellet is fully transferred to the transfer syringe 100, the transfer syringe 100 is removed from the syringe locking mechanism 76 and a standard hypodermic needle is attached to the transfer syringe 100 at the needle attachment 109 as seen in FIG. 14. The gauge and design of the needle for the transfer syringe may depend on the type of tissue delivered, the tissue the needle needs to penetrate to deliver the cells and the volume of the cells to be delivered. Saline and/or other chemicals may be added to reconstitute the cell pellet in the transfer syringe 100.

The transfer syringe 100 is then inserted into a patient in a specific location for delivery of the harvested cells for therapeutic purposes.

A person of ordinary skill in the art would appreciate the number, gauge, and design of the ports 259 may vary depending on the type of tissue harvested, the tissue the needle needs to penetrate to acquire the tissue, and the volume of the tissue needed.

The dual syringe may be used with a standard aspirating cannula as well with traditional access to the cells created through trocar use or surgical incision. Once the cells are harvested, the dual syringe is removed from the patient. The standard aspirating cannula is removed 270 from the harvesting syringe 10. The shaft 92 is unscrewed from the plunger head 91 and removed from the harvesting syringe 10. A standard syringe port cap is attached to the needle attachment 34 to seal inflow port 32. The dual syringe 1 is placed in a centrifuge and spun at approximately 500 to 2000 g forces for a period of 3 to 20 minutes. Centrifugation causes the aspirated cells to separate from the aspirated fluid. As a result of the funnel shape of the bottom wall 30, the cells, denser than the fluid, form a pellet on the bottom wall 30 near the outflow port 31. The valve 39 remains closed due to the positive pressure exerted from the outflow port 31 which prevents any of the contents of the barrel from migrating through pathway 38 and/or through the bottom port 77 of the spacer 70. The dual syringe 1 is removed from the centrifuge. The transfer plunger 110 is pulled away from the bottom end 105 which creates negative pressure within the interior cavity 108 of the transfer syringe 100. This negative pressure opens the valve 39 to allow cells of the pellet to move through the outflow port 31, through the pathway 38, through the interior cavity 74 of the spacer 70, through the top port 75, through the port 107 of the transfer syringe and into the interior cavity 108 of the transfer syringe 100. To adjust for the varying hydraulic pressure within the interior cavity 60 of the harvesting syringe 10, if necessary, the harvesting plunger may be manually depressed, after reattachment of the shaft 92, by the user in conjunction with user's pulling of the transfer plunger 110. Once the cell pellet is fully transferred to the transfer syringe 100, the transfer syringe 100 is removed from the syringe locking mechanism 76 and a standard hypodermic needle is attached to the transfer syringe 100 at the needle attachment 109 as seen in FIG. 14. The gauge and design of the needle for the transfer syringe may depend on the type of tissue delivered, the tissue the needle needs to penetrate to deliver the cells and the volume of the cells to be delivered. Saline and/or other chemicals may be added to reconstitute the cell pellet in the transfer syringe 100. The transfer syringe 100 is then inserted into a patient in a specific location for delivery of the harvested cells for therapeutic purposes.

The above device may be used for autologous stem cell transplantation in an office setting as described in FIG. 15. A healthcare provider may utilize local anesthetic at the specific harvesting site or general anesthetic for the harvesting of stem cells. Stem cell harvesting may occur through adipose tissue in a patient's abdominal region, or through adipose tissue in another adipose-rich region such as the inner thigh or through a patient's bone marrow. The healthcare provider utilizes the sterile dual syringe and attaches the percutaneous cannula 200. The healthcare provider inserts the dual syringe 1 with the percutaneous cannula 200 as described in FIG. 15 into the patient's abdomen and aspirates 50 to 60 milliliters of adipose tissue into the harvesting syringe 10. Centrifugation separates a cellular pellet rich in mesenchymal stem cells from the stromal vascular fraction. The mesenchymal stem cells are then transferred to the transfer syringe 100 as described in FIG. 15. The transfer syringe is removed from the harvesting syringe, a needle is attached as shown in FIG. 11, and then the mesenchymal stem cells are transplanted into the same patient for treatment of osteoarthritis, for assistance in wound healing, or for one or more of many other regenerative medicine uses. The procedure is accomplished in the same office visit for the patient.

In a preferred embodiment the harvesting syringe 10, transfer syringe 100, percutaneous cannula assembly 200, syringe port cap, and hypodermic needle 50 are sterile and stored in a single use sterile packaging kit. The packaged unit is designed for singular use for a single patient for transplantation of autologous tissue.

We claim:

1. A dual syringe assembly comprising:
    a first syringe having an open top end, a longitudinal sidewall forming a barrel, a bottom wall opposite said open top end and a flange member extending from said barrel forming a handle wherein said sidewall and said bottom wall define a cavity within said first syringe;
    a first port extending through said bottom wall and creating a fluid pathway with said cavity of said first syringe;
    a second port positioned at said bottom wall and creating a fluid pathway with said cavity;
    a plunger inserted into said cavity of said first syringe through said open end;
    a second syringe having an open top end, a longitudinal cylindrically-shaped sidewall forming a barrel, a bottom wall opposite said open top end and a flange member extending from said barrel forming a handle, wherein said sidewall and said bottom wall define a cavity within said second syringe;
    a port in said bottom wall of said second syringe creating a fluid pathway with said cavity of said second syringe;
    a plunger inserted into said cavity of said second syringe through said open end;
    a fluid pathway which directs flow from said cavity within said first syringe, through said second port of said first syringe, through said port of said second syringe and into said cavity of said second syringe; and
    a longitudinal groove in the exterior surface of said sidewall of said first syringe wherein a portion of said cylindrically-shaped sidewall of said second syringe is positioned within said groove.

2. A dual syringe assembly of claim 1 wherein said second port of said first syringe is positioned below said first port of said first syringe.

3. A dual syringe assembly of claim 1 wherein said groove extends along at least a portion of the length of said sidewall of said first syringe.

4. A dual syringe assembly of claim 2 wherein said second port extends through said bottom wall of said first syringe.

5. A dual syringe assembly of claim 3 further comprising:
    a spacer positioned in said groove wherein said spacer has a first end with a first port and a second end with a second port; and
    a channel disposed between said first and second ports wherein said first port of said spacer is fluidly connected with said second port of said first syringe and said second port of said spacer is fluidly connected with said port of said second syringe.

6. A dual syringe assembly of claim 5 wherein said first end of said spacer is aligned with said bottom wall of said first syringe.

7. A dual syringe assembly of claim 5 wherein said second syringe is attached to said second end of said spacer.

8. A dual syringe assembly of claim 5 further comprising a valve disposed between said second port of said first syringe and said first port of said spacer.

9. A dual syringe assembly of claim 2 wherein said bottom wall of said first syringe has an interior face that is sloped away from said top end from said first port to said second port.

10. A dual syringe assembly of claim 2 wherein said plunger of said first syringe comprises a shaft with a plunger head on one end and a handle on the opposing end wherein said shaft is removable from said plunger head.

11. A dual syringe assembly of claim 1 further comprising a valve disposed between said second port of said first syringe and said port of said second syringe.

12. A dual syringe assembly of claim 1 further comprising:
a needle hub comprising a syringe attachment member, cannula attachment member, and a hollow needle extending from said cannula attachment member and fluidly connected with said first port of said first syringe; and
a cannula having an opening on one end and an attachment member on the opposing end wherein said attachment member of said cannula is connected to said cannula attachment member of said needle hub; and said needle of said needle hub is positioned within said cannula and extends through said opening of said cannula;
wherein said syringe attachment member of said needle hub is attachable to and detachable from said first syringe.

13. A dual syringe assembly of claim 12 wherein said cannula is removable from said needle hub.

14. A dual syringe assembly of claim 12 wherein said cannula further comprises at least one port along the longitudinal axis.

15. A dual syringe assembly of claim 12 wherein said cannula tapers to said opening of said cannula.

16. A dual syringe assembly of claim 12 wherein said cannula is attachable to and detachable from said first syringe.

17. A dual syringe assembly of claim 1 further comprising:
a cannula having an opening on one end and an attachment member on the opposing end wherein said attachment member of said cannula is attachable to and detachable from said first syringe wherein said cannula is fluidly connected to said first port of said first syringe.

18. A dual syringe assembly of claim 17 wherein said cannula further comprises at least one port along the longitudinal axis.

19. A dual syringe assembly of claim 17 wherein said cannula tapers to said opening of said cannula.

20. A dual syringe assembly comprising
a first syringe having a sidewall forming a barrel of said first syringe, said barrel having a top end and a bottom end wherein said top end is open and a flange member extending from said barrel forming a handle;
a bottom wall of said first syringe enclosing said bottom end of said barrel of said first syringe wherein said sidewall and said bottom wall define a cavity within said first syringe;
a first port and a second port through said bottom wall, each of said ports creating a fluid pathway with said cavity of said first syringe;
wherein said bottom wall of said first syringe has an interior face that is sloped away from said top end from said first port to said second port; and
wherein said second port of said first syringe is positioned below said first port of said first syringe;
a plunger inserted into said cavity of said first syringe through said open end;
a second syringe having a sidewall forming a barrel of said second syringe, said barrel having a top end and a bottom end wherein said top end is open and a flange member extending from said barrel forming a handle;
a bottom wall of said second syringe enclosing said bottom end of said barrel of said second syringe wherein said sidewall and said bottom wall define a cavity within said second syringe;
a port in said bottom wall of said second syringe creating a fluid pathway with said cavity of said second syringe;
a plunger inserted into said cavity of said second syringe through said open end; and
a fluid pathway which directs flow from said cavity within said first syringe, through said second port of said first syringe, through said port of said second syringe and into said cavity of said second syringe.

21. A dual syringe assembly of claim 20 wherein said sidewall of said first syringe is shaped to form a longitudinal groove in said sidewall of said first syringe and at least a portion of said barrel of said second syringe is positioned within said groove.

22. A dual syringe assembly of claim 20 wherein said plunger of said first syringe comprises a shaft with a plunger head on one end and a handle on the opposing end wherein said shaft is removable from said plunger head.

23. A dual syringe assembly comprising
a first syringe having a sidewall and bottom wall that define a cavity having an open top end opposite said bottom wall;
a first port extending through said bottom wall and creating a fluid pathway with said cavity of said first syringe;
a second port positioned at said bottom wall and creating a fluid pathway with said cavity wherein said second port is positioned below said first port;
wherein said bottom wall of said first syringe has an interior face that is sloped away from said top end from said first port to said second port;
a plunger inserted into said cavity of said first syringe through said open end;
a second syringe having a sidewall and bottom wall that define a cavity having an open end opposite said bottom wall;
a port in said bottom wall of said second syringe creating a fluid pathway with said cavity of said second syringe;
a plunger inserted into said cavity of said second syringe through said open end; and
a fluid pathway which directs flow from said cavity within said first syringe, through said second port of said first syringe, through said port of said second syringe and into said cavity of said second syringe.

24. A dual syringe assembly of claim 23 wherein said sidewall of said first syringe is shaped to form a longitudinal groove in said sidewall of said first syringe and wherein at least a portion of said second syringe is positioned within said groove.

25. The dual syringe assembly of claim 23 wherein said second port extends through said bottom wall of said first syringe.

26. A dual syringe assembly of claim 23 wherein said plunger of said first syringe comprises a shaft with a plunger head on one end and a handle on the opposing end wherein said shaft is removable from said plunger head.

* * * * *